United States Patent
Greene, Jr. et al.

(10) Patent No.: US 6,602,261 B2
(45) Date of Patent: *Aug. 5, 2003

(54) FILAMENTOUS EMBOLIC DEVICE WITH EXPANSILE ELEMENTS

(75) Inventors: George R. Greene, Jr., Costa Mesa, CA (US); Gregory M. Cruise, Rancho Santa Margarita, CA (US); Michael Constant, Mission Viejo, CA (US); Brian J. Cox, Laguna Niguel, CA (US)

(73) Assignee: Microvention, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/867,340

(22) Filed: May 29, 2001

(65) Prior Publication Data

US 2002/0120276 A1 Aug. 29, 2002

Related U.S. Application Data (63) Continuation-in-part of application No. 09/542,145, filed on Apr. 4, 2000, now Pat. No. 6,299,619, which is a continuation-in-part of application No. 09/410,970, filed on Oct. 4, 1999, now Pat. No. 6,238,403.

(51) Int. Cl.$^7$ ................................................ A61F 11/00
(52) U.S. Cl. ........................................................ 606/108
(58) Field of Search ................................ 606/108, 191, 606/194, 195, 200

(56) References Cited

U.S. PATENT DOCUMENTS

| | | |
|---|---|---|
| 3,709,842 A | 1/1973 | Stoy et al. |
| 4,301,803 A | 11/1981 | Handa et al. |
| 4,365,621 A | 12/1982 | Brundin |

(List continued on next page.)

FOREIGN PATENT DOCUMENTS

| | | |
|---|---|---|
| WO | 97/48351 | 12/1997 |
| WO | 99/23954 | 5/1999 |
| WO | 99/56783 | 11/1999 |
| WO | 99/59479 | 11/1999 |
| WO | 99/65401 | 12/1999 |
| WO | 00/74577 | 12/2000 |
| WO | 01/06950 | 2/2001 |
| WO | WO 0139811 A1 | 6/2001 |

OTHER PUBLICATIONS

Vacanti, et al., "Tissue Engineering: The Design and Fabrication of Living Replacement Devices for Surgical Reconstruction and Transplantation," *The Lancet* (vol. 354, Supplement 1) pp. 32–34 (Jul.

(List continued on next page.)

*Primary Examiner*—Eduardo C. Robert
(74) *Attorney, Agent, or Firm*—Klein, O'Neill & Singh, LLP.

(57) ABSTRACT

An embolization device includes one or more expansible, hydrophilic embolizing elements non-releasably carried along the length of a filamentous carrier that is preferably made of a very thin, highly flexible filament or microcoil of nickel/titanium alloy. At least one expansile embolizing element is non-releasably attached to the carrier. A first embodiment includes a plurality of embolizing elements fixed to the carrier at spaced-apart intervals along its length. In a second embodiment, an elongate, continuous, coaxial embolizing element is non-releasably fixed to the exterior surface of the carrier, extending along a substantial portion of the length of the carrier proximally from a distal tip. In either of the embodiments, the embolizing elements may be made of a hydrophilic, macroporous, polymeric, hydrogel foam material. In the second embodiment, the elongate embolizing element is preferably made of a porous, environmentally-sensitive, expansile hydrogel that expands, after a predetermined time delay, in response to a change in an environmental parameter, such as pH or temperature.

34 Claims, 8 Drawing Sheets

U.S. PATENT DOCUMENTS

| | | | |
|---|---|---|---|
| 4,402,319 A | 9/1983 | Handa et al. | |
| 4,509,504 A | 4/1985 | Brundin | |
| 4,529,739 A | 7/1985 | Scott et al. | |
| 4,663,358 A | 5/1987 | Hyon et al. | |
| 5,120,349 A | 6/1992 | Stewart | |
| 5,122,136 A | 6/1992 | Guglielmi et al. | |
| 5,129,180 A | 7/1992 | Stewart | |
| 5,226,911 A | 7/1993 | Chee et al. | |
| 5,250,071 A | 10/1993 | Palermo | |
| 5,258,042 A | 11/1993 | Mehta | |
| 5,320,639 A | 6/1994 | Rudnick | |
| 5,350,397 A | 9/1994 | Palermo et al. | |
| 5,354,290 A | 10/1994 | Gross | |
| 5,456,693 A | 10/1995 | Conston et al. | |
| 5,522,822 A | 6/1996 | Phelps et al. | |
| 5,536,274 A | 7/1996 | Neuss | |
| 5,541,234 A | 7/1996 | Unger et al. | |
| 5,549,624 A | 8/1996 | Mirigian et al. | |
| 5,573,994 A | 11/1996 | Kabra et al. | |
| 5,582,619 A | 12/1996 | Ken | |
| 5,624,461 A | 4/1997 | Mariant | |
| 5,624,685 A | 4/1997 | Takahashi et al. | |
| 5,645,558 A | 7/1997 | Horton | |
| 5,672,634 A | 9/1997 | Tseng et al. | |
| 5,690,667 A | 11/1997 | Gia | |
| 5,690,671 A | 11/1997 | McGurk et al. | |
| 5,695,480 A | * 12/1997 | Evans et al. | 604/264 |
| 5,718,711 A | 2/1998 | Berenstein et al. | |
| 5,749,894 A | 5/1998 | Engelson | |
| 5,750,585 A | 5/1998 | Park et al. | |
| 5,752,974 A | 5/1998 | Rhee et al. | |
| 5,766,160 A | 6/1998 | Samson et al. | |
| 5,766,219 A | 6/1998 | Horton | |
| 5,797,953 A | 8/1998 | Tekulve | |
| 5,823,198 A | 10/1998 | Jones et al. | |
| 5,833,705 A | 11/1998 | Ken et al. | |
| 5,843,118 A | 12/1998 | Sepetka et al. | |
| 5,891,155 A | 4/1999 | Irie | |
| 5,891,192 A | 4/1999 | Murayama et al. | |
| 5,895,411 A | 4/1999 | Irie | |
| 5,911,717 A | 6/1999 | Jacobsen et al. | |
| 5,911,731 A | 6/1999 | Pham et al. | |
| 5,935,148 A | 8/1999 | Villar et al. | |
| 5,980,514 A | 11/1999 | Kupiecki et al. | |
| 5,980,554 A | 11/1999 | Lenker et al. | |
| 6,004,338 A | 12/1999 | Ken et al. | |
| 6,013,084 A | 1/2000 | Ken et al. | |
| 6,015,424 A | 1/2000 | Rosenbluth et al. | |
| 6,024,754 A | 2/2000 | Engelson | |
| 6,066,149 A | 5/2000 | Samson et al. | |
| 6,093,199 A | 7/2000 | Brown et al. | |
| 6,113,629 A | 9/2000 | Ken | |
| 6,143,007 A | 11/2000 | Mariant et al. | |
| 6,165,193 A | * 12/2000 | Greene, Jr. et al. | 606/191 |
| 6,187,024 B1 | 2/2001 | Boock et al. | |
| 6,187,027 B1 | 2/2001 | Mariant et al. | |
| 6,193,728 B1 | 2/2001 | Ken et al. | |
| 6,312,421 B1 | * 11/2001 | Boock | 606/194 |

OTHER PUBLICATIONS

Woerly, S. et al., "Intracerebral implantation of synthetic polymer/biopolymer matrix: a new perspective for brain repair," PubMed Query.

Zollikofer, Christoph et al., "Therapeutic Blockade of Arteries Using Compressed Ivalon[1]", *Department of Radiology, University of Minnesota Hospitals*, Radiology 136:635–640, Sep. 1980.

Zollikofer, Christoph, et al, "A Combination Of Stainless Steel Coil and Compressed Ivalon: A New Technique for Embolization of Large Arteries and Arteriovenous Fistulas", *Technical Notes*, vol. 138, pp. 229–231, Jan., 1981.

Dawson, Robert C., etal., "Treatment of Experimental Aneurysms Using Collagen–Coated Microcoils", *Neurosurgery*, vol. 36, No. 1, pp. 133–140 (Jan., 1995).

Langer, "Tissue Engineering: A new field and its challenges," *Pharmaceutical Research*, vol. 14, No. 7, pp. 840–841 (Jul., 1997).

Larsen, Nancy E., et al., "Hyland gel composition for percutaneous embolization," *Journal of Biomedical Materials Research*, vol. 25, 699–710 (1991).

Latchaw, R.E., M.D. et al., "Polyvinyl Foam Embolization of Vasular and Neoplastic Lesions of the Head, Neck, and Spine," *Dept of Radiology, University of Minnesota Hospitals*, Radiology 131:669–679, Jun. 1979.

Persidis, "Tissue Engineering," *Nature Biotechnology*, vol. 17, pp. 508–510 (May, 1999).

Soranzo, C., et al., "Evaluation of Two Hyaluronan Derivatives (Hyaff7 and ACP Sponges) For Bone Healing", *The $20^{th}$ Annual Meeting of the Society For Biomaterials*, Apr. 5–9, 1994, p. 99.

Tadavarthy, S. Murthy, et al., "Polyvinyl Alcohol (Ivalon)–A New Embolic Material," *Dept of Radiology, University of Minnesota Hospitals*, vol. 125, No. 3, Nov., 1975.

Chirila, T.V. et al., "Poly(2–hydroxyethyl methacrylate) sponges as implant materials: in vivo and in vitro evaluation of cellular invasion," *Biomaterials*, 1993, vol. 14 No. 1.

Edelman, Elazer R., "Controlled and modulated release of basic fibroblast growth factor", *Biomaterials*, Sep. 1991, vol. 12, pp. 619–662.

Hogg, Phillip J., et al., "Interaction of platelet–derived growth factor with thrombospondin 1", *Biochem J.*, (1997) 326, 709–716.

Hoekstra, Djoerd, "Hyaluronan–Modified Surfaces for Medical Devices", *Medical Device & Diagnostic Industry*, Feb., 1999, pp. 48–56.

Horàk, D. et al., "Hydrogels in endovascular embolization.II,Clinical use of spherical particles," *Biomaterials* (1986), vol. 7, Nov., pp. 467–470.

Horàk, D. et al., "New radiopaque polyHEMA–based hydrogel particles," *Journal of Biomedical Materials Research*, vol. 34, pp. 183–188, (1997).

* cited by examiner

FILAMENTOUS EMBOLIC DEVICE WITH EXPANSILE ELEMENTS

CROSS REFERENCE TO RELATED APPLICATIONS

This application is a Continuation-in-Part of application Ser. No. 09/542,145, filed Apr. 4, 2000, now U.S. Pat. No. 6,299,619 issued Oct. 9, 2001, which is a Continuation-in-Part of application Ser. No. 09/410,970, filed Oct. 4, 1999, now U.S. Pat. No. 6,238,403 issued May 29, 2001.

FEDERALLY SPONSORED RESEARCH OR DEVELOPMENT

Not Applicable

BACKGROUND OF THE INVENTION

The present invention relates to the field of methods and devices for the embolization of vascular aneurysms and similar vascular abnormalities. More specifically, the present invention relates to an embolic device that is inserted into a vascular site such as an aneurysm to create an embolism therein and a method for embolizing a vascular site using the device.

The embolization of blood vessels is desired in a number of clinical situations. For example, vascular embolization has been used to control vascular bleeding, to occlude the blood supply to tumors, and to occlude vascular aneurysms, particularly intracranial aneurysms. In recent years, vascular embolization for the treatment of aneurysms has received much attention. Several different treatment modalities have been employed in the prior art. U.S. Pat. No. 4,819,637—Dormandy, Jr. et al., for example, describes a vascular embolization system that employs a detachable balloon delivered to the aneurysm site by an intravascular catheter. The balloon is carried into the aneurysm at the tip of the catheter, and it is inflated inside the aneurysm with a solidifying fluid (typically a polymerizable resin or gel) to occlude the aneurysm. The balloon is then detached from the catheter by gentle traction on the catheter. While the balloon-type embolization device can provide an effective occlusion of many types of aneurysms, it is difficult to retrieve or move after the solidifying fluid sets, and it is difficult to visualize unless it is filled with a contrast material. Furthermore, there are risks of balloon rupture during inflation and of premature detachment of the balloon from the catheter.

Another approach is the direct injection of a liquid polymer embolic agent into the vascular site to be occluded. One type of liquid polymer used in the direct injection technique is a rapidly polymerizing liquid, such as a cyanoacrylate resin, particularly isobutyl cyanoacrylate, that is delivered to the target site as a liquid, and then is polymerized in situ. Alternatively, a liquid polymer that is precipitated at the target site from a carrier solution has been used. An example of this type of embolic agent is a cellulose acetate polymer mixed with bismuth trioxide and dissolved in dimethyl sulfoxide (DMSO). Another type is ethylene vinyl alcohol dissolved in DMSO. On contact with blood, the DMSO diffuses out, and the polymer precipitates out and rapidly hardens into an embolic mass that conforms to the shape of the aneurysm. Other examples of materials used in this "direct injection" method are disclosed in the following U.S. Pat. No. 4,551,132—Pásztor et al.; U.S. Pat. No. 4,795,741—Leshchiner et al.; U.S. Pat. No. 5,525,334—Ito et al.; and U.S. Pat. No. 5,580,568—Greff et al.

The direct injection of liquid polymer embolic agents has proven difficult in practice. For example, migration of the polymeric material from the aneurysm and into the adjacent blood vessel has presented a problem. In addition, visualization of the embolization material requires that a contrasting agent be mixed with it, and selecting embolization materials and contrasting agents that are mutually compatible may result in performance compromises that are less than optimal. Furthermore, precise control of the deployment of the polymeric embolization material is difficult, leading to the risk of improper placement and/or premature solidification of the material. Moreover, once the embolization material is deployed and solidified, it is difficult to move or retrieve.

Another approach that has shown promise is the use of thrombogenic microcoils. These microcoils may be made of a biocompatible metal alloy (typically platinum and tungsten) or a suitable polymer. If made of metal, the coil may be provided with Dacron fibers to increase thrombogenicity. The coil is deployed through a microcatheter to the vascular site. Examples of microcoils are disclosed in the following U.S. Pat. No. 4,994,069—Ritchart et al.; U.S. Pat. No. 5,133,731—Butler et al.; U.S. Pat. No. 5,226,911—Chee et al.; U.S. Pat. No. 5,312,415—Palermo; U.S. Pat. No. 5,382,259—Phelps et al.; U.S. Pat. No. 5,382,260—Dormandy, Jr. et al.; U.S. Pat. No. 5,476,472—Dormandy, Jr. et al.; U.S. Pat. No. 5,578,074—Mirigian; U.S. Pat. No. 5,582,619—Ken; U.S. Pat. No. 5,624,461—Mariant; U.S. Pat. No. 5,645,558—Horton; U.S. Pat. No. 5,658,308—Snyder; and U.S. Pat. No. 5,718,711—Berenstein et al.

The microcoil approach has met with some success in treating small aneurysms with narrow necks, but the coil must be tightly packed into the aneurysm to avoid shifting that can lead to recanalization. Microcoils have been less successful in the treatment of larger aneurysms, especially those with relatively wide necks. A disadvantage of microcoils is that they are not easily retrievable; if a coil migrates out of the aneurysm, a second procedure to retrieve it and move it back into place is necessary. Furthermore, complete packing of an aneurysm using microcoils can be difficult to achieve in practice.

A specific type of microcoil that has achieved a measure of success is the Guglielmi Detachable Coil ("GDC"), described in U.S. Pat. No. 5,122,136—Guglielmi et al. The GDC employs a platinum wire coil fixed to a stainless steel delivery wire by a solder connection. After the coil is placed inside an aneurysm, an electrical current is applied to the delivery wire, which electrolytically disintegrates the solder junction, thereby detaching the coil from the delivery wire. The application of the current also creates a positive electrical charge on the coil, which attracts negatively-charged blood cells, platelets, and fibrinogen, thereby increasing the thrombogenicity of the coil. Several coils of different diameters and lengths can be packed into an aneurysm until the aneurysm is completely filled. The coils thus create and hold a thrombus within the aneurysm, inhibiting its displacement and its fragmentation.

The advantages of the GDC procedure are the ability to withdraw and relocate the coil if it migrates from its desired location, and the enhanced ability to promote the formation of a stable thrombus within the aneurysm. Nevertheless, as in conventional microcoil techniques, the successful use of the GDC procedure has been substantially limited to small aneurysms with narrow necks.

Still another approach to the embolization of an abnormal vascular site is the injection into the site of a biocompatible hydrogel, such as poly (2-hydroxyethyl methacrylate) ("pHEMA" or "PHEMA"); or a polyvinyl alcohol foam ("PAF"). See, e.g., Horak et al., "Hydrogels in Endovascular Embolization. II. Clinical Use of Spherical Particles", *Biomaterials*, Vol. 7, pp. 467–470 (Nov., 1986); Rao et al., "Hydrolysed Microspheres from Cross-Linked Polymethyl Methacrylate", *J. Neuroradiol.*, Vol. 18, pp. 61–69 (1991); Latchaw et al., "Polyvinyl Foam Embolization of Vascular and Neoplastic Lesions of the Head, Neck, and Spine", *Radiology*, Vol. 131, pp. 669–679 (June, 1979). These materials are delivered as microparticles in a carrier fluid that is injected into the vascular site, a process that has proven difficult to control.

A further development has been the formulation of the hydrogel materials into a preformed implant or plug that is installed in the vascular site by means such as a microcatheter. See, e.g., U.S. Pat. No. 5,258,042—Mehta. These types of plugs or implants are primarily designed for obstructing blood flow through a tubular vessel or the neck of an aneurysm, and they are not easily adapted for precise implantation within a sac-shaped vascular structure, such as an aneurysm, so as to fill substantially the entire volume of the structure.

U.S. Pat. No. 5,823,198—Jones et al. discloses an expansible PVA foam plug that is delivered to the interior of an aneurysm at the end of a guidewire. The plug comprises a plurality of pellets or particles that expand into an open-celled structure upon exposure to the fluids within the aneurysm so as to embolize the aneurysm. The pellets are coated with a blood-soluble restraining agent to maintain them in a compressed state and attached to the guidewire until delivered to the aneurysm. Because there is no mechanical connection between the pellets and the guidewire (other than the relatively weak temporary bond provided by the restraining agent), however, premature release and migration of some of the pellets remains a possibility.

There has thus been a long-felt, but as yet unsatisfied need for an aneurysm treatment device and method that can substantially fill aneurysms of a large range of sizes, configurations, and neck widths with a thrombogenic medium with a minimal risk of inadvertent aneurysm rupture or blood vessel wall damage. There has been a further need for such a method and device that also allow for the precise locational deployment of the medium, while also minimizing the potential for migration away from the target location. In addition, a method and device meeting these criteria should also be relatively easy to use in a clinical setting. Such ease of use, for example, should preferably include a provision for good visualization of the device during and after deployment in an aneurysm.

SUMMARY OF THE INVENTION

Broadly, an embolization device, according to a first aspect of the present invention, comprises one or more expansible, hydrophilic embolizing elements non-releasably carried along the length of a filamentous carrier. In a first preferred embodiment, the carrier is a suitable length of very thin, highly flexible filament of nickel/titanium alloy (Nitinol). A plurality of embolizing elements are spaced along the length of the carrier and are separated from each other on the carrier by radiopaque spacers in the form of highly flexible microcoils made of platinum or platinum/tungsten alloy, as in the thrombogenic microcoils of the prior art, as described above.

In a second preferred embodiment, the carrier comprises a continuous length of highly flexible, hollow microcoil made of a biocompatible metal (preferably platinum or platinum/tungsten alloy), with an optional core in the form of a continuous length of thin, highly flexible metal wire, preferably of a shape memory metal alloy such as Nitinol. Alternatively, the carrier may be a suitable length of flexible wire, cable, braid, or other construction that yields the desired flexibility. The carrier is preferably made of a biocompatible metal so as to be visible by means of X-rays or other visualization techniques known in the art, but it also may be made of a suitable polymer that is visible (or is rendered visible) through any of the known visualization methods. The carrier should have sufficient column strength to allow the device to be pushed through a microcatheter.

In the second preferred embodiment, an elongate, continuous, coaxial embolizing element is non-releasably fixed to the exterior surface of the carrier, extending along a substantial portion of the length of the carrier proximally from a distal tip.

In either of the preferred embodiments, the embolizing elements may be made of a hydrophilic, macroporous, polymeric, hydrogel foam material, in particular a swellable foam matrix formed as a macroporous solid comprising a foam stabilizing agent and a polymer or copolymer of a free radical polymerizable hydrophilic olefin monomer cross-linked with up to about 10% by weight of a multiolefin-functional cross-linking agent. Such a material is described in U.S. Pat. No. 5,750,585—Park et al., the disclosure of which is incorporated herein by reference. The material may be modified, or provided with additives, to make the implant visible by conventional imaging techniques.

In the second preferred embodiment, the elongate coaxial embolizing element is preferably made of a porous, environmentally-sensitive, expansile hydrogel, of the type described in prior co-pending U.S. patent application Ser. No. 09/783,762, assigned to the assignee of this application and of the invention disclosed and claimed herein. Application Ser. No. 09/783,762 (the disclosure of which is incorporated herein by reference) discloses hydrogels that undergo controlled volumetric expansion in response to changes in such environmental parameters as pH or temperature. These hydrogels are prepared by forming a liquid mixture that contains (a) at least one monomer and/or polymer, at least a portion of which is sensitive to changes in an environmental parameter; (b) a cross-linking agent; and (c) a polymerization initiator. If desired, a porosigen (e.g., NaCl, ice crystals, or sucrose) may be added to the mixture, and then removed from the resultant solid hydrogel to provide a hydrogel with sufficient porosity to permit cellular ingrowth. The controlled rate of expansion is provided through the incorporation of ethylenically unsaturated monomers with ionizable functional groups (e.g., amines, carboxylic acids). For example, if acrylic acid is incorporated into the crosslinked network, the hydrogel is incubated in a low pH solution to protonate the carboxylic acids. After the excess low pH solution is rinsed away and the hydrogel dried, the hydrogel can be introduced through a microcatheter filled with saline at physiological pH or with blood. The hydrogel cannot expand until the carboxylic acid groups deprotonate. Conversely, if an amine-containing monomer is incorporated into the crosslinked network, the hydrogel is incubated in a high pH solution to deprotonate the amines. After the excess high pH solution is rinsed away and the hydrogel dried, the hydrogel can be introduced through a microcatheter filled with saline at physiological pH or with blood. The hydrogel cannot expand until the amine groups protonate.

Alternatively, in the second preferred embodiment, the elongate coaxial embolizing element may be in the form of a stretch-resistant outer layer applied to the exterior of the carrier along a substantial portion of the length of the carrier. The stretch-resistant outer layer is preferably formed of an expansile material, such as those described above, but it may also be formed of any stretch-resistant, biocompatible polymer, such as, for example, polyurethane, polyester, polytetrafluoroethylene (PTFE), nylon, polymethylmethacrylate (PMMA), and silicone.

A second aspect of the present invention is a method for embolizing a vascular site, comprising, in the preferred embodiment the steps of: (a) passing a microcatheter intravascularly so that its distal end is introduced into a target vascular site; (b) passing a vaso-occlusive device through the microcatheter into the target vascular site so that the vaso-occlusive device assumes a three-dimensional configuration that fills a portion of the volume of the target vascular site; (c) providing a vascular embolization device comprising at least one expansible embolizing element non-releasably connected to a filamentous carrier; (d) passing the embolization device through the microcatheter so that it emerges from the distal end of the microcatheter into the target vascular site; and (e) expanding the embolizing element or elements in situ so that at least about 30%, and preferably more than about 40%, of the total the volume of the target vascular site is filled, while maintaining the connection between the embolizing element or elements and the carrier.

Preferably, the vaso-occlusive device is of the type that is initially in the form of an elongate, flexible, filamentous element for delivery through the microcatheter, and that assumes a three-dimensional geometry upon installation in the target vascular site. One such device is the above-described GDC (U.S. Pat. No. 5,122,136—Guglielmi et al., the disclosure of which is incorporated herein by reference). Other such devices are describe in, for example, U.S. Pat. No. 5,766,219—Horton; U.S. Pat. No. 5,690,671—McGurk et al.; and U.S. Pat. No. 5,911,731—Pham et al., the disclosures of which are incorporated herein by reference. Still other types of vaso-occlusive devices known in the art may also perform satisfactorily in this method.

In an alternative embodiment of the method of the present invention, the method comprises the steps of: (a) deploying an intravascular device to a position in a blood vessel adjacent to a target vascular site; (b) providing a vascular embolization device comprising at least one expansible embolizing element non-releasably connected to a filamentous carrier; (c) passing a microcatheter intravascularly so that the distal end of the microcatheter passes through the intravascular device into the target vascular site; (d) passing the embolization device through the microcatheter so that it emerges from the distal end of the microcatheter into the target vascular site; and (e) expanding the embolizing element or elements in situ substantially to fill the volume of the target vascular site while maintaining the connection between the embolizing element or elements and the carrier.

It is understood that the step of providing the embolization device may follow the step of passing the microcatheter intravascularly.

In this alternative embodiment of the method aspect of the present invention, the intravascular device may be of the type disclosed in U.S. Pat. No. 5,980,514—Kupiecki et al., the disclosure of which is incorporated herein by reference. This intravascular device comprises a filamentous element that is introduced by a microcatheter to the juncture of an aneurysm or the like, and that then assumes the configuration of a coil adjacent the neck of the aneurysm.

In some instances, the step of passing a vaso-occlusive device or an intravascular device through the microcatheter to the target vascular site may be omitted.

The embolization bodies or elements, in the preferred embodiment, have an initial configuration in the form of small, substantially cylindrical "micropellets" of small enough outside diameter to fit within the microcatheter. The bodies are hydrophilically expansible into an expanded configuration in which they substantially conform to and fill the vascular site.

The present invention provides a number of significant advantages. Specifically, the present invention provides an effective vascular embolization device that can be deployed within a vascular site with excellent locational control, and with a lower risk of vascular rupture, tissue damage, or migration than with prior art devices. Furthermore, the embolization device effects a conformal fit within the site that promotes effective embolization, and yet its ability to be delivered to the site through a microcatheter facilitates precise and highly controllable deployment. In addition, the essentially filamentous initial configuration of the embolization device, whereby it readily conforms to the interior dimensions of the vascular site, allows it to be used effectively to embolize vascular sites having a wide variety of sizes, configurations, and (in the particular case of aneurysms) neck widths. These and other advantages will be readily appreciated from the detailed description that follows.

DETAILED DESCRIPTION OF THE INVENTION

The Embolization Device: First Preferred Embodiment

Figure 1:
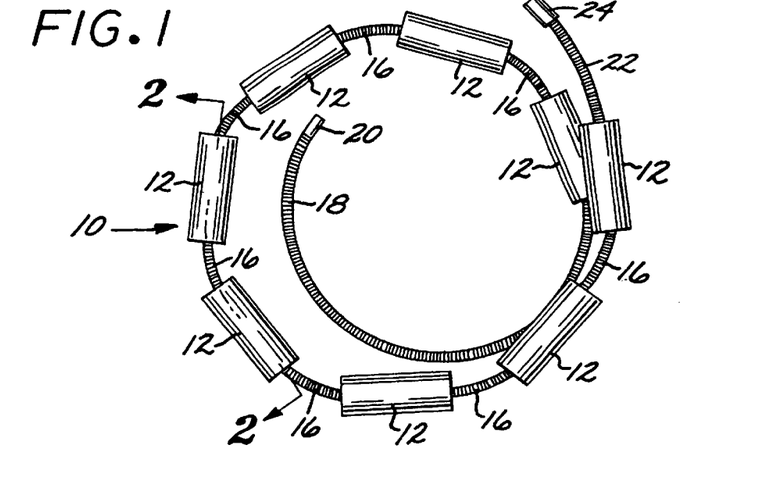
FIG. 1 is an elevational view of a vascular embolization device in accordance with a first preferred embodiment of the invention.
Figure 2:
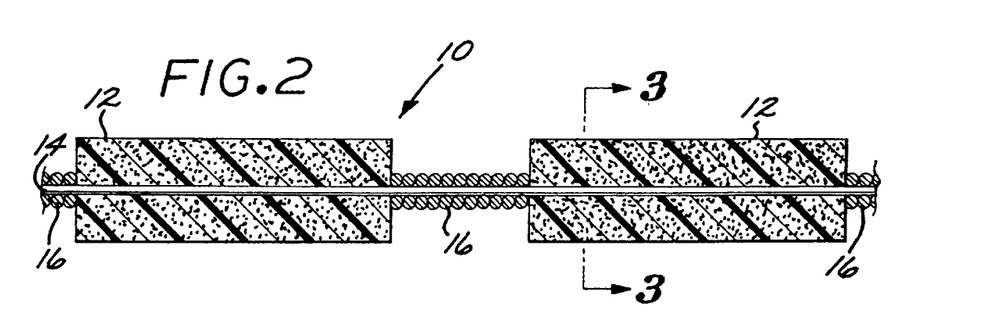
FIG. 2 is a cross-sectional view taken along line 2—2 of FIG. 1.
Figure 3:
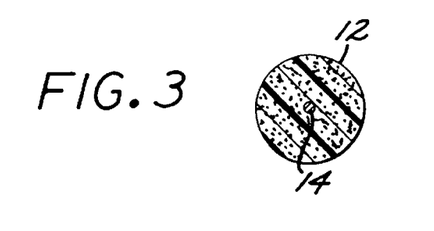
FIG. 3 is a cross-sectional view taken along line 3—3 of FIG. 2.

A vascular embolization device 10, in accordance with a first preferred embodiment of the present invention, is shown in FIGS. 1, 2 and 3. In the preferred embodiment, the embolization device 10 comprises a plurality of embolizing bodies, each configured as a substantially cylindrical "micropellet" 12, located at spaced intervals along a filamentous carrier 14. The number of micropellets 12 will vary, depending on the 13 length of the carrier 14, which, turn, will depend on the size of the vascular site to be embolized. For a large vascular site, for example, eight to twelve micropellets may be used, although an even larger number may be used if necessary. In some applications (e.g., very small aneurysms), as few as one or two micropellets may be used.

Also carried on the carrier 14 is a plurality of highly flexible microcoil spacers 16, each of which is disposed between and separates a pair of micropellets 12. The carrier 14 has a distal portion on which is carried a relatively long distal microcoil segment 18 that is retained in place by a distal retention member 20. The carrier 14 has a proximal portion on which is carried a relatively long proximal microcoil segment 22. The proximal end of the device 10 is terminated by a hydrogel linkage element 24, to be described below. The spacers 16, the distal microcoil segment 18, and the proximal microcoil segment 22 are all highly flexible, and they are preferably made of platinum or platinum/tungsten wire, which has the advantages of being biocompatible and radiopaque. The micropellets 12 are non-releasably carried on the carrier 14. They may be fixed in place on the filamentous carrier 14, either mechanically or by a suitable biocompatible, water-insoluble adhesive, or they may be simply strung loosely on the carrier 14 between successive spacers 16.

The micropellets 12 are preferably formed of a biocompatible, macroporous, hydrophilic hydrogel foam material, in particular a water-swellable foam matrix formed as a macroporous solid comprising a foam stabilizing agent and a polymer or copolymer of a free radical polymerizable hydrophilic olefin monomer cross-linked with up to about 10% by weight of a multiolefin-functional cross-linking agent. A suitable material of this type is described in U.S. Pat. No. 5,570,585—Park et al., the disclosure of which is incorporated herein by reference.

Another suitable material for the micropellets 12 is a porous hydrated polyvinyl alcohol (PVA) foam gel prepared from a polyvinyl alcohol solution in a mixed solvent consisting of water and a water-miscible organic solvent, as described, for example, in U.S. Pat. No. 4,663,358—Hyon et al., the disclosure of which is incorporated herein by reference. Other suitable PVA structures are described in U.S. Pat. No. 5,823,198—Jones et al. and U.S. Pat. No. 5,258,042—Mehta, the disclosures of which are incorporated herein by reference. Another suitable material is a collagen foam, of the type described in U.S. Pat. No. 5,456,693—Conston et al., the disclosure of which is incorporated herein by reference. Still another suitable material is PHEMA, as discussed in the references cited above. See, e.g., Horak et al., supra, and Rao et al., supra.

The preferred foam material, as described in the above-referenced patent to Park et al., has a void ratio of at least about 90%, and its hydrophilic properties are such that it has a water content of at least about 90% when fully hydrated. In the preferred embodiment, each of the embolizing micropellets 12 has an initial diameter of not more than about 0.5 mm prior to expansion in situ, with an expanded diameter of at least about 3 mm. To achieve such a small size, the micropellets 12 may be compressed to the desired size from a significantly larger initial configuration. The compression is performed by squeezing or crimping the micropellets 12 in a suitable implement or fixture, and then "setting" them in the compressed configuration by heating and/or drying. Each of the micropellets 12 is swellable or expansible to many times (at least about 25 times, preferably about 70 times, and up to about 100 times) its initial (compressed) volume, primarily by the hydrophilic absorption of water molecules from an aqueous solution (e.g., resident blood plasma and/or injected saline solution), and secondarily by the filling of its pores with blood. Also, the micropellets 12 may be coated with a water-soluble coating (not shown), such as a starch or a suitable polymer, to provide a time-delayed expansion. Another alternative is to coat the micropellets 12 with a temperature-sensitive coating that disintegrates in response to normal human body temperature. See, e.g., U.S. Pat. No. 5,120,349—Stewart et al. and U.S. Pat. No. 5,129,180—Stewart.

The foam material of the embolizing micropellet 12 may advantageously be modified, or provided with additives, to make the device 10 visible by conventional imaging techniques. For example, the foam can be impregnated with a water-insoluble radiopaque material such as barium sulfate, as described by Thanoo et al., "Radiopaque Hydrogel Microspheres", *J. Microencapsulation*, Vol. 6, No. 2, pp. 233–244 (1989). Alternatively, the hydrogel monomers can be copolymerized with radiopaque materials, as described in Horák et al., "New Radiopaque PolyHEMA-Based Hydrogel Particles", *J. Biomedical Materials Research*, Vol. 34, pp. 183–188(1997).

The micropellets 12 may optionally include bioactive or therapeutic agents to promote thrombosis, cellular ingrowth, and/or epithelialization. See, e.g, Vacanti et al., "Tissue Engineering: The Design and Fabrication of Living Replacement Devices for Surgical Reconstruction and Transplantation," *The Lancet* (Vol. 354, Supplement 1), pp.

32–34 (July, 1999); Langer, "Tissue Engineering: A New Field and Its Challenges," *Pharmaceutical Research*, Vol. 14., No. 7, pp. 840–841 (July, 1997); Persidis, "Tissue Engineering," *Nature Biotechnology*, Vol. 17, pp. 508–510 (May, 1999).

The filamentous carrier 14 is preferably a length of nickel/titanium wire, such as that marketed under the trade name "Nitinol". Wire of this alloy is highly flexible, and it has an excellent "elastic memory", whereby it can be formed into a desired shape to which it will return when it is deformed. In a preferred embodiment of the invention, the wire that forms the carrier 14 has a diameter of approximately 0.04 mm, and it is heat-treated to form a multi-looped structure that may assume a variety of three-dimensional shapes, such as a helix, a sphere, or an ovoid when unconstrained (as disclosed, for example, in U.S. Pat. No. 5,766,219—Horton, the disclosure of which is incorporated herein by reference). Preferably, the intermediate portion of the carrier 14 (i.e., the portion that includes the micropellets 12) and the proximal portion (that carries the proximal microcoil segment 22) are formed into loops having a diameter of approximately 6 mm, while the distal portion (that carries the distal microcoil segment 18) may have a somewhat greater diameter (e.g., approximately 8–10 mm). The carrier 14 may be formed of a single wire, or it may be formed of a cable or braided structure of several ultra-thin wires.

In another embodiment, the carrier 14 may be made of a thin filament of a suitable polymer, such as a PVA, that is formed in a looped structure. The polymer may be impregnated with a radiopaque material (e.g., barium sulfate or particles of gold, tantalum, or platinum), or it may enclose a core of nickel/titanium wire. Alternatively, the carrier 14 may be constructed as a "cable" of thin polymer fibers that includes fibers of an expansile polymer, such as polyvinyl alcohol (PVA), at spaced intervals to form the micropellets 12.

Still another alternative construction for the carrier 14 is a continuous length of microcoil. In such an embodiment, the micropellets 12 would be attached at spaced intervals along the length of the carrier 14.

Figure 8:
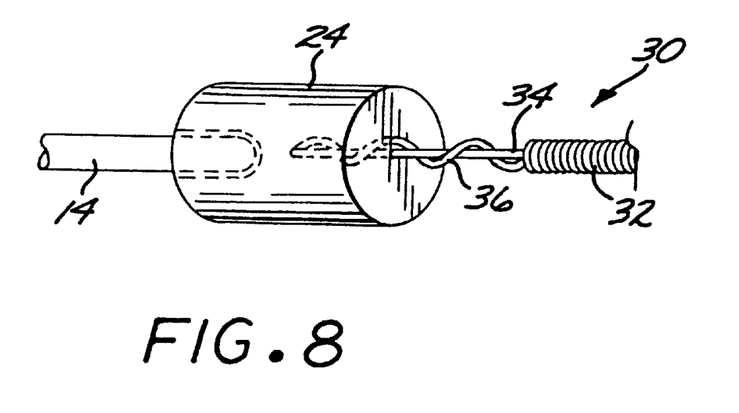
FIG. 8 is a detailed perspective view of mechanism by which the embolization device of the present invention is preferably attached to the distal end of a deployment instrument.
Figure 9:
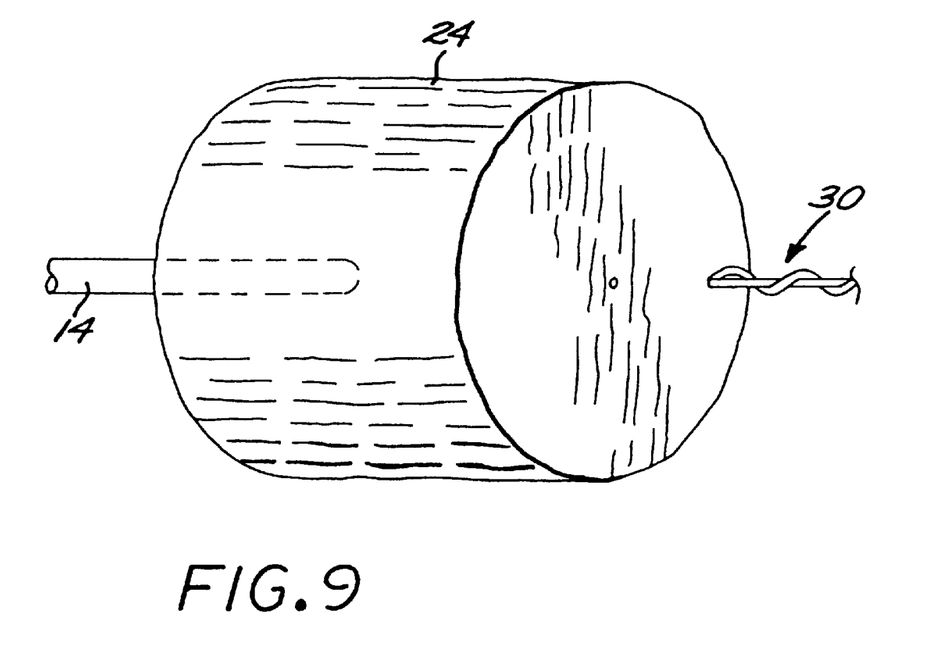
FIG. 9 is a detailed perspective view, similar to that of FIG. 8, showing the embolization device of the present invention after it has been separated from the deployment instrument.

As shown in FIGS. 1, 8, and 9, the hydrogel linkage element 24 is advantageously made of the same material as the micropellets 12. Indeed, the most proximal of the micropellets 12 may function as the linkage element 24. The linkage element 24 is attached to the proximal end of the carrier 14 by a suitable biocompatible adhesive. The purpose of the linkage element 24 is to removably attach the device 10 to a deployment instrument 30 (FIGS. 8 and 9). The deployment instrument 30 comprises a length of platinum or platinum/tungsten microcoil outer portion 32 with a flexible wire core 34 of the same or a similar metal. The deployment instrument 30 has a distal portion 36 at which the microcoil outer portion 32 has coils that are more distantly-spaced (i.e., have a greater pitch).

As shown in FIG. 8, the device 10 is initially attached to the deployment instrument 30 by means of the linkage element 24. Specifically, the linkage element is installed, in a compressed state, so that it encompasses and engages both the proximal end of the embolization device 10 and the distal portion 36 of the deployment instrument 30. Thus, in the compressed state, the linkage element 24 binds the deployment instrument 30 and the embolization device 10 together. As shown in FIG. 9, and as will be described in detail below, after the device 10 is deployed in a vascular site, the linkage element 24 expands greatly, thereby loosening its grip on the distal portion 36 of the deployment instrument 30, and thus allowing the embolization device 10 to be separated from the deployment instrument 30 by pulling the latter proximally out of and away from the linkage element 24.

The Embolization Device: Second Preferred Embodiment

FIGS. 14 through 23 illustrate an embolization device in accordance with a second preferred embodiment of the present invention. Referring first to FIGS. 14 through 17, a device 100 in accordance with this second embodiment comprises an elongate, flexible, filamentous carrier 102 on which an expansile embolizing element 104 is non-releasably carried. The carrier 102 is preferably formed from a continuous length of hollow microcoil 106, made from a suitable metal such as platinum, gold, tungsten, or tantalum, or a metallic alloy, such as stainless steel or Nitinol. Of these materials, platinum and Nitinol are preferred. The microcoil is formed with tightly-packed coils, so that there is little or no spacing between adjacent coils. The carrier 102 may also include a filamentous core 108 extending axially through the microcoil 106. The core 108 is a thin metal wire, preferably made of a shape memory metal such as Nitinol. The device 100 includes a distal portion comprising an outer coil 110 coaxially surrounding the microcoil 106, and terminating in a rounded distal tip 112. A hydrogel linkage element (not shown), of the type described above and illustrated in FIGS. 8 and 9, may advantageously be provided at the proximal end of the carrier.

Figures 14, 15, 16:
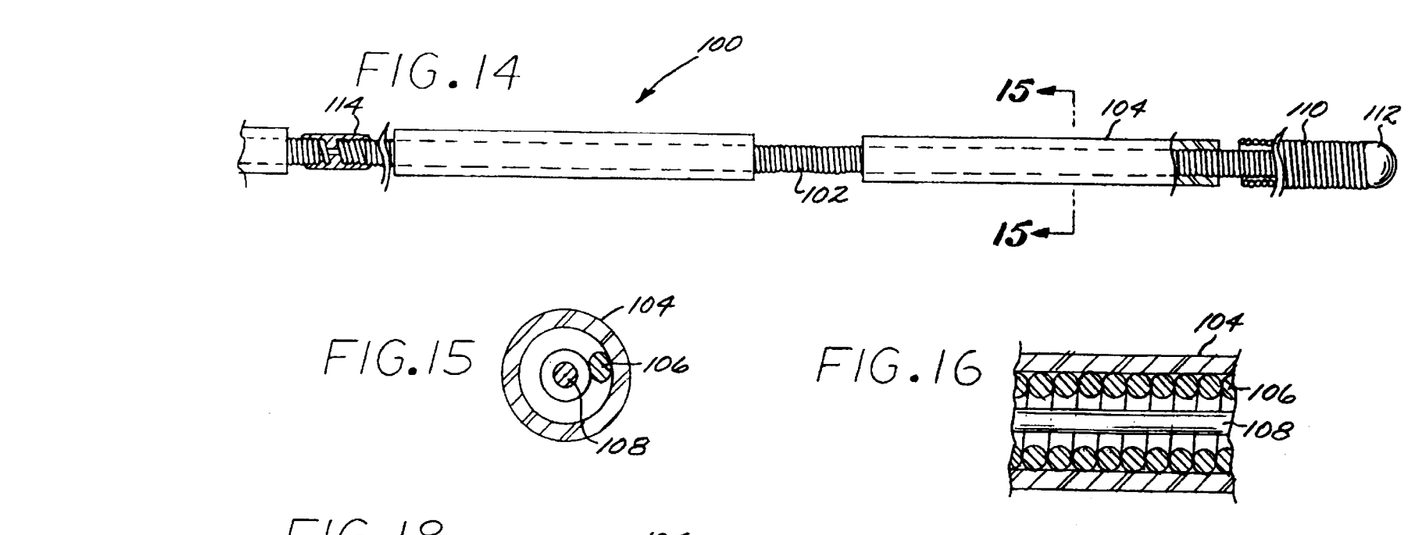
FIG. 14 is an elevational view, partially in section, of an embolic device in accordance with a second preferred embodiment of the invention, showing the device in its normal or non-expanded state.
FIG. 15 is a cross-sectional view taken along line 15—15 of FIG. 14.
FIG. 16 is a detailed axial cross-sectional view of a portion of the device shown in FIG. 14.

The carrier 102 may, alternatively, be made of any of the materials described above with respect to the carrier of the first preferred embodiment. While it is preferably in the configuration of a microcoil, it may also be formed as a single strand of metal wire or polymeric filament, or as a multi-strand braid or cable of metal wire or polymeric filament. The carrier should have a column strength sufficient to allow it to be pushed through a microcatheter, as mentioned above.

The expansile embolizing element 104 is advantageously formed as a hydrogel layer covering a substantial portion of the length of the carrier 102. The embolizing element 104 may be made of any of the materials used in the embolizing elements of the above-described first preferred embodiment. Advantageously, however, the embolizing element 104 of this second embodiment is preferably formed of a porous, environmentally-sensitive, expansile hydrogel of the type described in prior co-pending U.S. patent application Ser. No. 09/783,762 (the disclosure of which is incorporated herein by reference). For the convenience of the reader, a brief description of a suitable formulation of a preferential hydrogel is set forth below.

Specifically, the hydrogels described in the above-referenced prior application are of a type that undergoes controlled volumetric expansion in response to changes in such environmental parameters as pH or temperature. These hydrogels are prepared by forming a liquid mixture that contains (a) at least one monomer and/or polymer, at least a portion of which is sensitive to changes in an environmental parameter; (b) a cross-linking agent; and (c) a polymerization initiator. If desired, a porosigen (e.g., NaCl, ice crystals, or sucrose) may be added to the mixture, and then removed from the resultant solid hydrogel to provide a hydrogel with sufficient porosity to permit cellular ingrowth. The controlled rate of expansion is provided through the incorporation of ethylenically unsaturated monomers with ionizable functional groups (e.g., amines, carboxylic acids). For example, if acrylic acid is incorporated into the crosslinked network, the hydrogel is incubated in a low pH solution to protonate the carboxylic acids. After the excess low pH solution is rinsed away and the hydrogel dried, the hydrogel can be introduced through a microcatheter filled with saline at physiological pH or with blood. The hydrogel cannot expand until the carboxylic acid groups deprotonate. Conversely, if an amine-containing monomer is incorporated into the crosslinked network, the hydrogel is incubated in a high pH solution to deprotonate amines. After the excess high pH solution is rinsed away and the hydrogel dried, the hydrogel can be introduced through a microcatheter filled with saline at physiological pH or with blood. The hydrogel cannot expand until the amine groups protonate.

More specifically, in a preferred formulation of the hydrogel, the monomer solution is comprised of ethylenically unsaturated monomers, an ethylenically unsaturated crosslinking agent, a porosigen, and a solvent. At least a portion, preferably 10%–50%, and more preferably 10%–30%, of the monomers selected must be pH sensitive. The preferred pH sensitive monomer is acrylic acid. Methacrylic acid and derivatives of both acids will also impart pH sensitivity. Since the mechanical properties of hydrogels prepared exclusively with these acids are poor, a monomer to provide additional mechanical properties should be selected. A preferred monomer for providing mechanical properties is acrylamide, which may be used in combination with one or more of the above-mentioned pH sensitive monomers to impart additional compressive strength or other mechanical properties. Preferred concentrations of the monomers in the solvent range from 20% w/w to 30% w/w.

The crosslinking agent can be any multifunctional ethylenically unsaturated compound, preferably N,N'-methylenebisacrylamide. If biodegradation of the hydrogel material is desired, a biodegradable crosslinking agent should be selected. The concentrations of the crosslinking agent in the solvent should be less than about 1% w/w, and preferably less than about 0.1% w/w.

The porosity of the hydrogel material is provided by a supersaturated suspension of a porosigen in the monomer solution. A porosigen that is not soluble in the monomer solution, but is soluble in the washing solution can also be used. Sodium chloride is the preferred porosigen, but potassium chloride, ice, sucrose, and sodium bicarbonate can also be used. It is preferred to control the particle size of the porosigen to less than about 25 microns, more preferably less than about 10 microns. The small particle size aids in the suspension of the porosigen in the solvent. Preferred concentrations of the porosigen range from about 5% w/w to about 50% w/w, more preferably about 10% w/w to about 20% w/w, in the monomer solution. Alternatively, the porosigen can be omitted and a non-porous hydrogel can be fabricated.

The solvent, if necessary, is selected based on the solubilities of the monomers, crosslinking agent, and porosigen. If a liquid monomer (e.g. 2-hydroxyethyl methacrylate) is used, a solvent is not necessary. A preferred solvent is water, but ethyl alcohol can also be used. Preferred concentrations of the solvent range from about 20% w/w to about 80% w/w, more preferably about 50% w/w to about 80% w/w.

The crosslink density substantially affects the mechanical properties of these hydrogel materials. The crosslink density (and hence the mechanical properties) can best be manipulated through changes in the monomer concentration, crosslinking agent concentration, and solvent concentration. The crosslinking of the monomer can be achieved through reduction-oxidation, radiation, and heat. Radiation crosslinking of the monomer solution can be achieved with ultraviolet light and visible light with suitable initiators or ionizing radiation (e.g. electron beam or gamma ray) without initiators. A preferred type of crosslinking initiator is one that acts via reduction-oxidation. Specific examples of such red/ox initiators that may be used in this embodiment of the invention are ammonium persulfate and N,N,N',N'-tetramethylethylenediamine.

After the polymerization is complete, the hydrogen is washed with water, alcohol or other suitable washing solution(s) to remove the porosigen(s), any unreacted, residual monomer(s) and any unincorporated oligomers. Preferably this is accomplished by initially washing the hydrogel in distilled water.

As discussed above, the control of the expansion rate of the hydrogel is achieved through the protonation/deprotonation of ionizable functional groups present on the hydrogel network. Once the hydrogel has been prepared and the excess monomer and porosigen have been washed away, the steps to control the rate of expansion can be performed.

In embodiments where pH sensitive monomers with carboxylic acid groups have been incorporated into the hydrogel network, the hydrogel is incubated in a low pH solution. The free protons in the solution protonate the carboxylic acid groups on the hydrogel network. The duration and temperature of the incubation and the pH of the solution influence the amount of control on the expansion rate. Generally, the duration and temperature of the incubation are directly proportional to the amount of expansion control, while the solution pH is inversely proportional. It has been determined that the water content of the treating solution also affects the expansion control. In this regard, the hydrogel is able to expand more in the treating solution and it is presumed that an increased number of carboxylic acid groups are available for protonation. An optimization of water content and pH is required for maximum control on the expansion rate. After the incubation is concluded, the excess treating solution is washed away and the hydrogel material is dried. The hydrogel treated with the low pH solution has been observed to dry down to a smaller dimension than the untreated hydrogel. This is a desired effect since delivery of these hydrogel materials through a microcatheter is desired.

If pH sensitive monomers with amine groups were incorporated into the hydrogel network, the hydrogel is incubated in high pH solution. Deprotonation occurs on the amine groups of the hydrogel network at high pH. The duration and temperature of the incubation, and the pH of the solution, influence the amount of control on the expansion rate. Generally, the duration, temperature, and solution pH of the incubation are directly proportional to the amount of expansion control. After the incubation is concluded, the excess treating solution is washed away and the hydrogel material is dried.

As shown in FIG. 14, an embolic device 100 in accordance with this second embodiment may include more than one elongate expansile embolizing elements 104. Also, if desired for a particular application, two or more embolizing devices 100 can be joined end-to-end at a juncture 114 formed by a weld or a solder joint.

Figure 17:
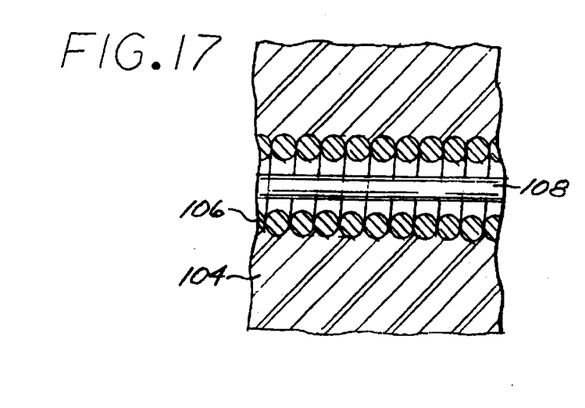
FIG. 17 is a view similar to that of FIG. 16, showing the device of FIG. 14 in its expanded state after deployment in a vascular site.
Figure 18:
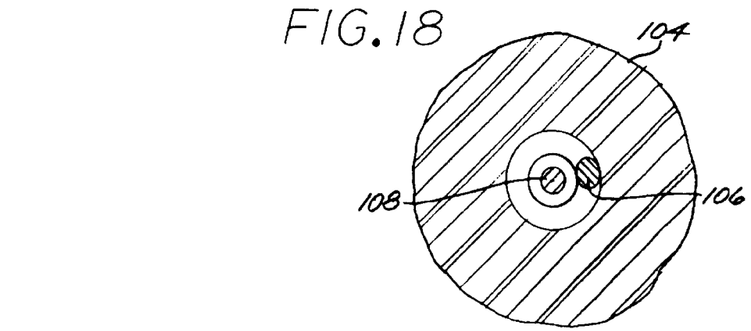
FIG. 18 is a view similar to that of FIG. 15, showing the device of FIG. 14 in its expanded state after deployment in a vascular site.

FIGS. 14, 15, and 16 show the device 100 with the embolizing elements 104 in their non-expanded state. Each embolizing element 104 assumes a tubular configuration in the form of a coating or layer on the exterior surface of the carrier 102. FIGS. 17 and 18 show an embolizing element 104 in its expanded state after deployment in a vascular site.

If made from the environmentally-sensitive hydrogel described above, the expansion is a reaction to the pH and/or temperature experienced in the vascular site. The expansion begins between about 1 minute and about 30 minutes after deployment, and preferably about 15 minutes after deployment. This delayed expansion allows the physician sufficient time to reposition and even withdraw the device without the need for a restraining agent, encapsulating layer, or a non-aqueous carrier fluid. When fully expanded, the embolizing element 104 has an expanded volume that is between about two times and about 100 times its non-expanded volume, and preferably between about 5 times and about 25 times its non-expanded volume.

Figure 19:
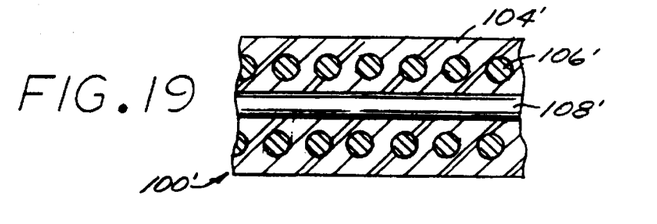
FIG. 19 is a partial axial cross-sectional view of a first modified form of an embolic device in accordance with the second preferred embodiment of the present invention, showing the device in its normal or non-expanded state.
Figure 20:
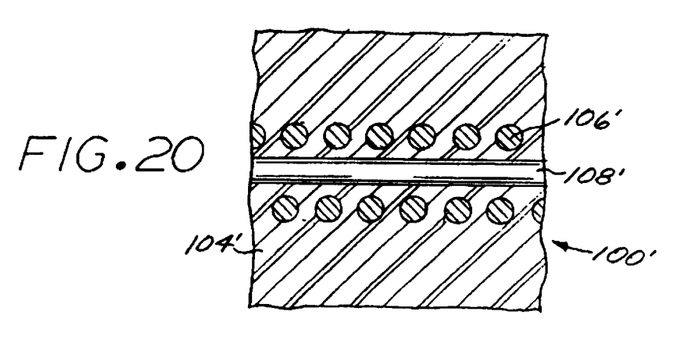
FIG. 20 is a view similar to that of FIG. 19, showing the device of FIG. 19 in its expanded state after deployment in a vascular site.

A first modification of this second preferred embodiment is shown in FIGS. 19 and 20. As shown, a modified embolic device 100' comprises an elongate, flexible, filamentous carrier. The carrier comprises an elongate, hollow microcoil 106' that is similar to the microcoil 106 shown in FIGS. 14–17, except that it has significant spaces between adjacent coils. Like the device 100 of FIGS. 14–17, the carrier of the device 100' may advantageously include a central axial core 108', formed of a thin, flexible wire. An expansile embolizing element 104', made of any of the above-described hydrogels, is formed on the carrier so that it resides between adjacent coils of the microcoil 106', thereby encapsulating them. FIG. 19 shows the embolizing element 104' in its non-expanded state, while FIG. 20 shows it in its expanded state, after deployment.

Figure 21:
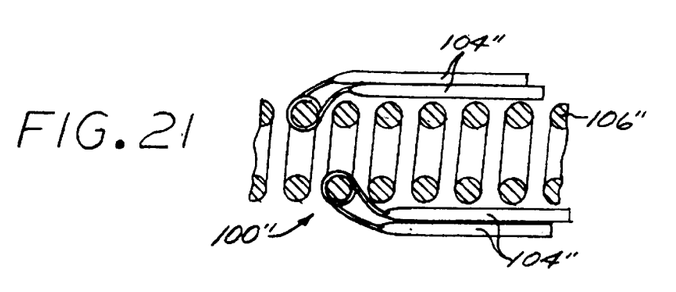
FIG. 21 is a partial axial cross-sectional view of a second modified form of an embolic device in accordance with the second preferred embodiment of the present invention, showing the device in its normal or non-expanded state.
Figure 22:
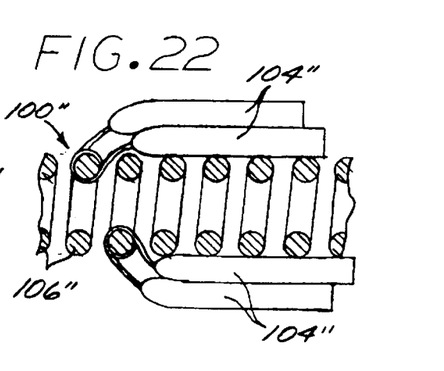
FIG. 22 is a view similar to that of FIG. 21, showing the device of FIG. 21 in its expanded state after deployment in a vascular site.

Another modification of the second preferred embodiment is shown in FIGS. 21 and 22. An embolic device 100" in accordance with this version comprises an elongate, filamentous carrier, preferably in the form of a hollow, flexible microcoil 106". Although the carrier is shown without a wire core, it is understood that a wire core may be included, as described above. In this version, a plurality of expansile embolizing elements 104" are formed as fibers or threads that are attached to the microcoil 106" at spaced-apart intervals along its length. Each of the expansile embolizing elements 104" is preferably made of an environmentally-sensitive hydrogel, of the type described in the prior co-pending application described above, although the hydrogel described in the U.S. Pat. No. 5,750,585—Park et al., supra, may also be used, as well as any of the other hydrogel materials described above in connection with the first preferred embodiment of the embolic device. FIG. 21, shows the embolizing elements 104" in their non-expanded state, while FIG. 22 shows them in their expanded state after deployment.

Figure 23:
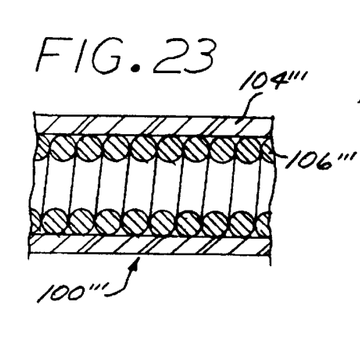
FIG. 23 is a detailed axial cross-sectional view of a third modified form of an embolic device in accordance with the second preferred embodiment of the present invention.

Still another modification of the second preferred embodiment is shown in FIG. 23. An embolic device 100''' in accordance with this version comprises an elongate, filamentous carrier, preferably in the form of a hollow, flexible microcoil 106'''. The carrier may include a wire core, although one is not shown in the drawing. This version includes an elongate coaxial embolizing element 104''' that is in the form of a stretch-resistant outer layer applied to the exterior of the microcoil 106''' along a substantial portion of the its length. The stretch-resistant outer layer is preferably formed of an expansile polymer, such as those described above, but it may also be formed of any stretch-resistant, biocompatible polymer, such as, for example, polyurethane, polyester, polytetrafluoroethylene (PTFE), nylon, polymethylmethacrylate (PMMA), and silicone.

The Method for Embolizing a Vascular Site

One method of embolizing a vascular site using either the embolization device 10 (first preferred embodiment) or the embolizing device 100 (second preferred embodiment) is illustrated in FIGS. 4 through 7. This method will be described with reference to the embolic device 10 of the first preferred embodiment, but it will be appreciated that this method is equally applicable to the device 100 of the second preferred embodiment.

Figure 4:
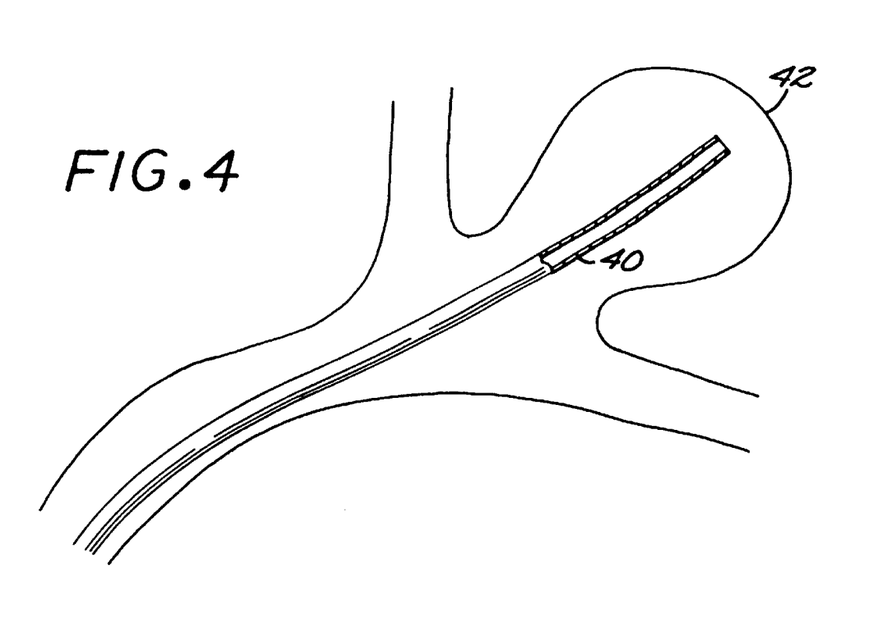
FIGS. 4 through 7 are semischematic views showing the steps in a method of embolizing a vascular site (specifically, an aneurysm) in accordance with one embodiment of the embolizing method aspect of the present invention.
Figure 5:
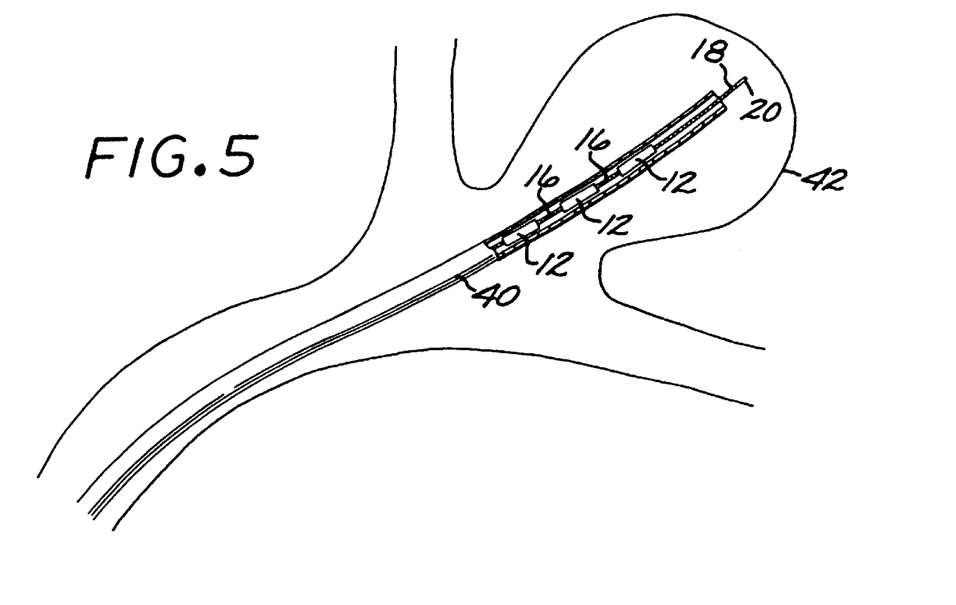
Figure 6:
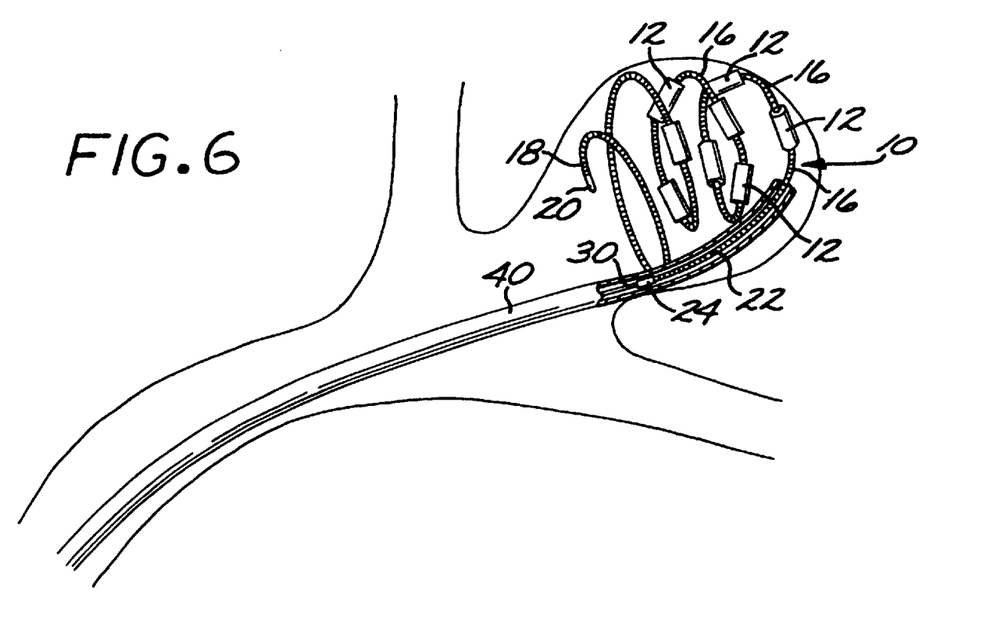

First, as shown in FIG. 4, a microcatheter 40 is threaded intravascularly, by known methods, until its distal end is located within the targeted vascular site (here, an aneurysm 42). Briefly described, this threading operation is typically performed by first introducing a catheter guidewire (not shown) along the desired microcatheter path, and then feeding the microcatheter 40 over the catheter guidewire until the microcatheter 40 is positioned adjacent the distal aspect of the dome of the aneurysm, as shown in FIG. 4. The catheter guidewire is then removed. Then, as shown in FIGS. 5 and 6, the embolization device 10, which is attached to the distal end of the deployment instrument 30, as described above, is passed axially through the microcatheter 40, using the deployment instrument 30 to push the device 10 through the microcatheter 40 until the device 10 is clear from the distal end of the microcatheter 40 and fully deployed within the aneurysm 42 (FIG. 6), filling the aneurysm from its distal aspect. The deployment procedure is facilitated by the visualization of the embolization device 10 that is readily accomplished due to its radiopaque components, as described above.

In the first preferred embodiment, the embolization bodies or micropellets 12, in their compressed configuration, have a maximum outside diameter that is less than the inside diameter of the microcatheter 40, so that the embolization device 10 can be passed through the microcatheter 40. The micropellets 12 are preferably compressed and "set", as described above, before the device 10 is inserted into the microcatheter 40. When inserting the device 10 into the microcatheter 40, a biocompatible, substantially non-aqueous fluid, such as polyethylene glycol, may be injected into the microcatheter 40 to prevent premature expansion of the device 10 due to hydration, and to reduce friction with the interior of the microcatheter 40.

As shown in FIG. 6, when the embolization device 10 is exposed from the microcatheter 40 into the interior of the vascular site 42, the pores of the embolizing bodies or micropellets 12, and of the linkage element 22, begin to absorb aqueous fluid from the blood within the vascular site 42 to release their "set", allowing these elements to begin assuming their expanded configuration. The expansion can be enhanced and accelerated by injecting saline solution through the microcatheter 40. The expansion of the linkage element 24 allows the embolization device 10 to be separated from the deployment instrument 30, as described above, and the deployment instrument 30 can then be removed. Also, the elastic memory of the carrier 14 causes it to resume its original looped configuration once it is released from the confines of the microcatheter 40. Thus, almost immediately upon its release into the vascular site (aneurysm) 42, the embolization device begins to occupy a significant portion of the volume of the aneurysm 42.

Figure 7:
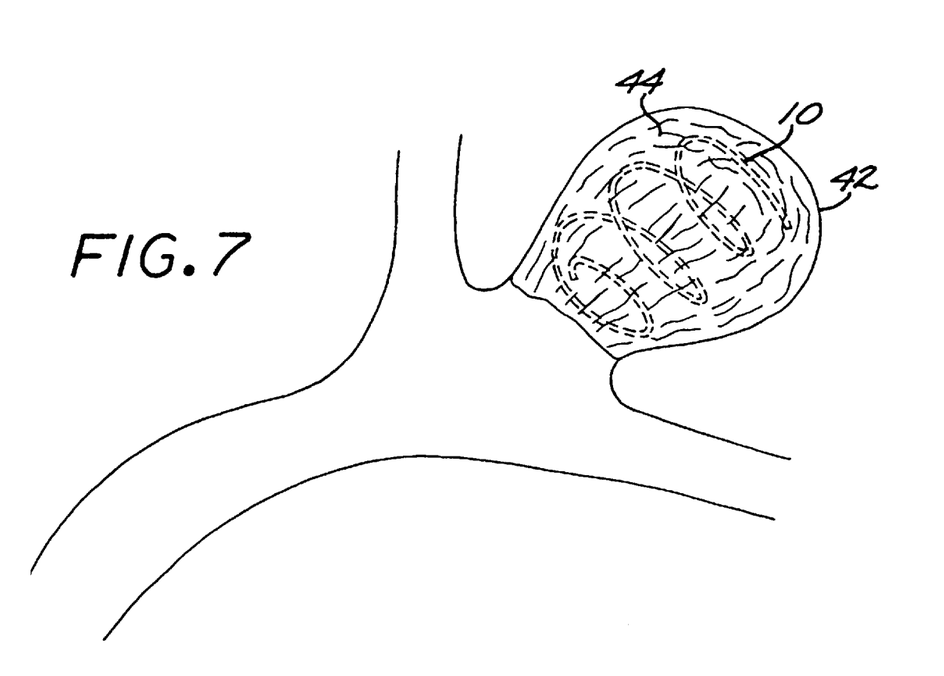

If the micropellets 12 are of a hydrophilic material, they then continue to expand in situ due to hydrophilic hydration of the material, as well as from the filling of their pores with blood. If the embolizing bodies 12 are of a non-hydrophilic material, their expansion is due to the latter mechanism only. In either case, the result, as shown in FIG. 7, is the substantially complete filling of the interior of the aneurysm 42 with the expanded embolizing bodies or micropellets 12, whereby a substantially conformal embolizing implant 44 is formed that substantially fills the interior of the aneurysm 42. The micropellets 12, being non-releasably carried the carrier 14 and fixed in place thereon, stay on the carrier during their expansion. Thus, the chance of a micropellet separating from the carrier and migrating out of the vascular site is minimized.

In the second preferred embodiment, the embolizing element 104 is not compressed in its initial configuration. Rather, it initially has a configuration in which its outside diameter is small enough to pass through the typical microcatheter. Once deployed within the target vascular site, the embolizing element 104 expands solely by hydration.

It may be advantageous, prior to performing the procedural steps described above, preliminarily to visualize the aneurysm 42, by conventional means, to obtain a measurement (or at least an approximation) of its volume. Then, a device 10 of the appropriate size can be selected that would expand to fill the measured or estimated volume.

Figure 10:
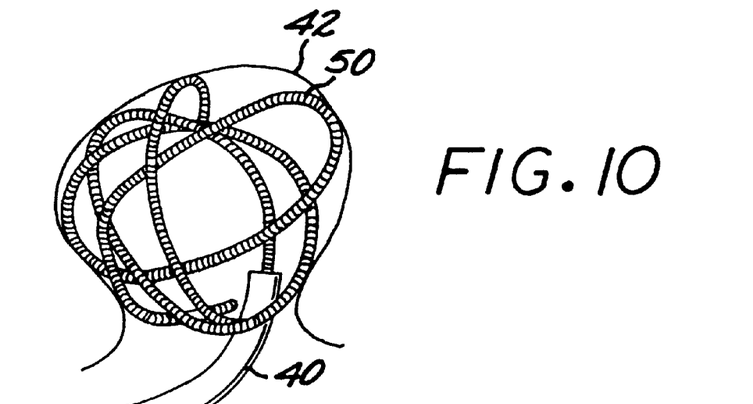
FIGS. 10, 11, and 12 are semischematic views showing steps that, in addition to those illustrated in FIGS. 4–7, constitute a method of embolizing a vascular site in accordance with a preferred embodiment of the embolizing method aspect of the present invention.
Figure 11:
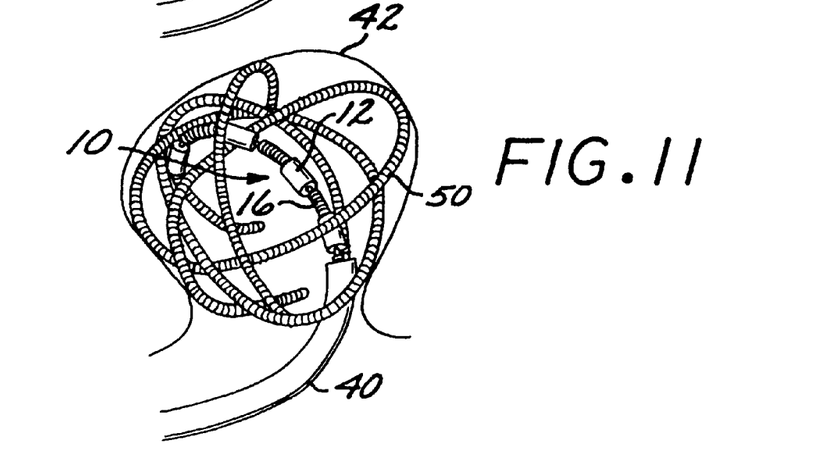
Figure 12:
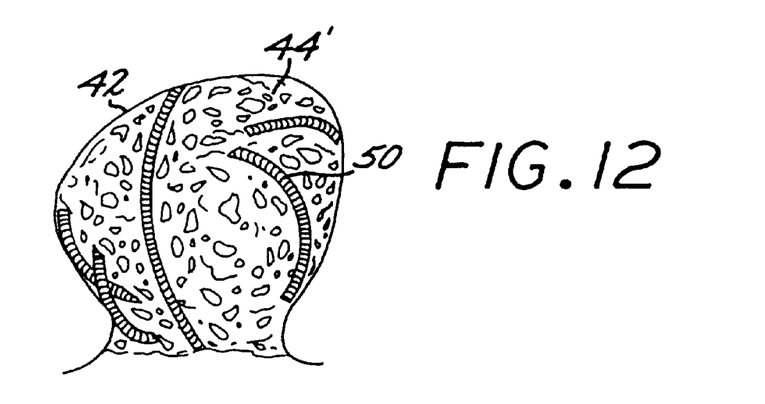

A preferred method of embolizing a target vascular site using the embolization device 10 will be understood with reference to FIGS. 10–12, along with FIGS. 4–7 (discussed above). In this preferred embodiment of the method, the passing of a microcatheter 40 intravascularly until its distal end is introduced into a target vascular site (FIG. 4) is followed by the step of passing a vaso-occlusive device 50 through the microcatheter 40 into the target vascular site (e.g., the aneurysm 42) so that the vaso-occlusive device 50 assumes a three-dimensional configuration that fills a portion of the interior volume of the target vascular site 42, as shown in FIG. 10. The deployed vaso-occlusive device 50 forms a "cage" within the aneurysm 42 that provides a matrix for improved retention of the expansible embolizing bodies or micropellets 12 of the embolization device 10. The embolization device 10 is then passed through the microcatheter 40, as described above, and as shown in FIG. 11, to enter the aneurysm 42 within the voids left by the vaso-occlusive device 50. Finally, the embolizing bodies or micropellets 12 are expanded, as described above, and as shown in FIG. 12, whereby a substantially conformal embolizing implant 44' is formed that fills a substantial portion of the interior volume of the aneurysm 42. Specifically, at least about 30%, and preferably at least about 40% of the interior volume is filled, and, it is believed that in some situations, as much as about 80% to 90% of the interior volume may be filled.

Preferably, the vaso-occlusive device 50 is of the type that is initially in the form of an elongate, flexible, filamentous element for delivery through the microcatheter, and that assumes a three-dimensional geometry (either by elastic behavior or by shape memory) upon installation in the target vascular site. Such devices are describe in, for example, U.S. Pat. No. 5,122,136—Guglielmi et al.; U.S. Pat. No. 5,766,219—Horton; U.S. Pat. No. 5,690,671—McGurk et al.; and U.S. Pat. No. 5,911,731—Pham et al., the disclosures of which are incorporated herein by reference. Still other types of vaso-occlusive devices known in the art may also perform satisfactorily in this method. For example, a stent-like device like that shown in U.S. Pat. No. 5,980,554—Lenker et al. may be employed Alternatively, the vaso-occlusive device 50 may be designed or installed only to enter the space near the opening or "neck" of the aneurysm. In any case, the purpose of the vaso-occlusive device 50 in this method is to present a structural framework that helps retain the embolization device 10 in place within the target vascular site.

Figure 13:
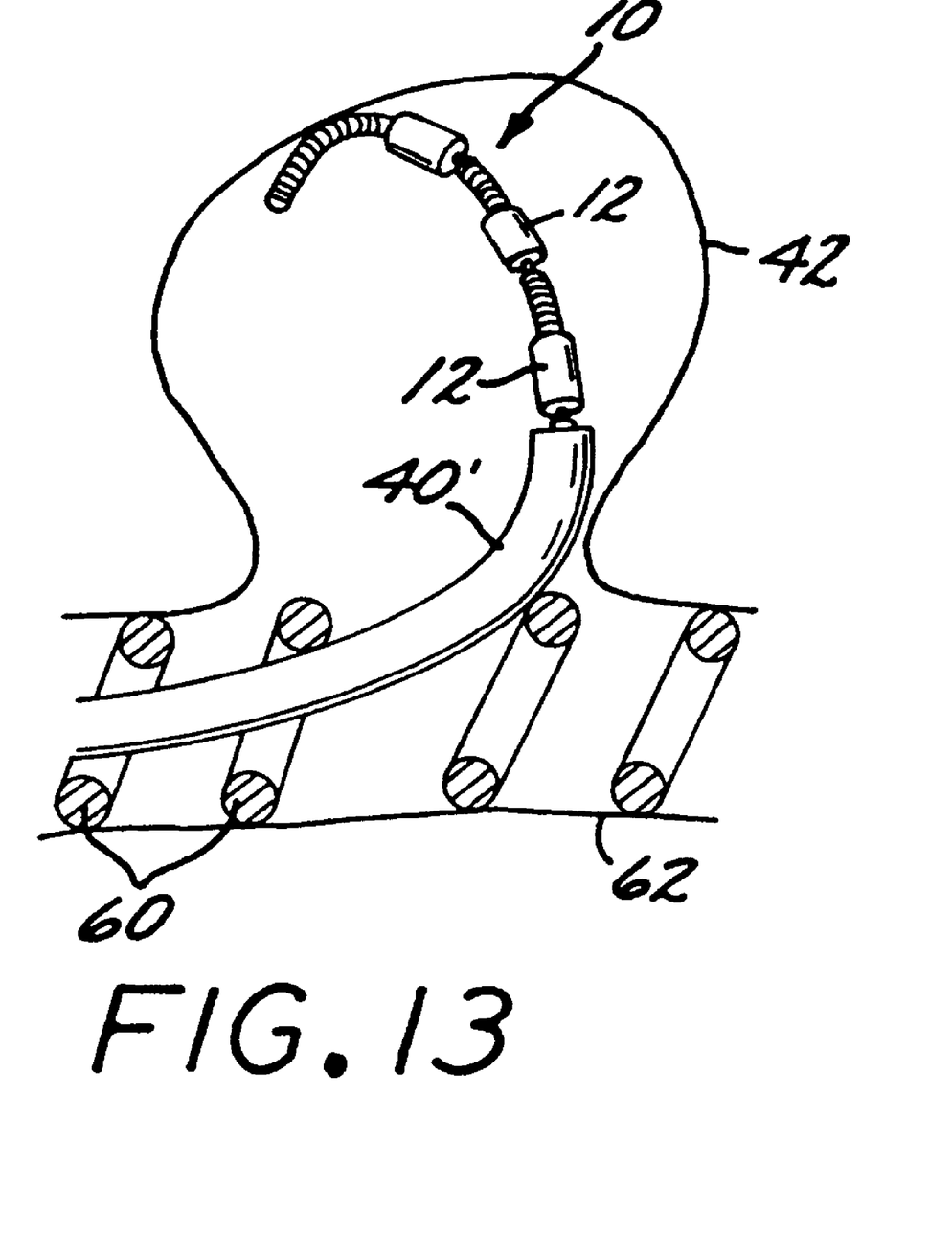
FIG. 13 is a semischematic view showing a step in a method of embolizing a vascular site in accordance with an alternative embodiment of the embolizing method aspect of the present invention.

An alternative embodiment of the method of the present invention will be understood with reference to FIG. 13. In this alternative embodiment, the method includes the preliminary step of deploying an intravascular device 60 to a position in a blood vessel 62 adjacent to a target vascular site 42. A microcatheter 40' is passed intravascularly so that its distal end passes through the intravascular device 60 into the target vascular site 42. The embolization device 10 is passed through the microcatheter 40' so that it emerges from the distal end of the microcatheter 40' into the target vascular site 42, and the embolizing elements 12 are then expanded in situ, as described above, substantially to fill the volume of the target vascular site 42 (as shown in FIGS. 7 and 12).

It is understood that the step of deploying an intravascular device to a position in a blood vessel adjacent to a target vascular site would include any substeps necessary for such deployment. For example, if the intravascular device 60 is of the type disclosed in U.S. Pat. No. 5,980,514—Kupiecki et al. (the disclosure of which is incorporated herein by reference), the deployment step would comprise the substeps of (i) passing of a microcatheter intravascularly so that its distal end is located adjacent the target vascular site; (ii) passing the intravascular device through the microcatheter until it emerges from the distal end of the microcatheter; and (iii) allowing the intravascular device to assume a three-dimensional configuration adjacent to the target vascular site. In this case, either the microcatheter used for deploying the intravascular device could be removed and then another microcatheter used to install the embolization device, or the intravascular deployment microcatheter could be repositioned for the introduction of the embolization device.

In this alternative method, the intravascular device presents an obstruction that at least partially blocks the juncture between the target vascular site and the blood vessel (e.g., the neck of an aneurysm). Thus, the intravascular device helps retain the embolization device in its proper position within the target vascular site.

It will be apparent that the method of using the second preferred embodiment of the device will be substantially similar to the above-described method.

Although the embolic device in accordance with the present invention has been described above for use in embolizing aneurysms, other applications will readily suggest themselves. For example, it can be used to treat a wide range of vascular anomalies, such as arteriovenous malformations and arteriovenous fistulas. Certain tumors may also be treated by the embolization of vascular spaces or other soft tissue voids using the present invention.

While preferred embodiments of the invention have been described above, a number of variations and modifications may suggest themselves to those skilled in the pertinent arts. For example, the initial shape and number of embolizing bodies or elements may be varied, as well as the length of the carrier. Furthermore, other mechanisms may be found for removably attaching the embolization device to the deployment wire. One such alternative attachment mechanism may be a transition polymer joint that loosens when heated by contact with blood or by a low-level electric current. These and other variations and modifications are considered within the spirit and scope of the invention, as described in the claims that follow.

What is claimed is:

1. A vascular embolization device, comprising:
   an elongate, flexible, filamentous carrier; and
   an embolizing element non-releasably fixed to the carrier, the embolizing element being formed from an expansile polymer that expands in response to a change in an environmental parameter selected from the group consisting of temperature and pH after a predetermined time interval.

2. The embolization device of claim 1, wherein the polymer is a porous hydrogel.

3. The embolization device of claim 1, wherein the embolizing element comprises an elongate, continuous, coaxial embolyzing element non-releasably fixed to the exterior surface of the carrier along a substantial portion of the length of the carrier.

4. The embolization device of claim 1, wherein the embolizing element comprises a plurality of expansile polymer fibers attached to the carrier.

5. The embolization device of claim 1, wherein the embolizing element is radiopaque.

6. The embolization device of claim 1, wherein the carrier is configured in the form of a multi-looped structure that may assume a three-dimensional shape when unconstrained.

7. The embolization device of claim 6, wherein the three-dimensional shape is selected from the group consisting of a sphere, a helix, and an ovoid.

8. A vascular embolization device, comprising:
   an elongate, flexible, filamentous carrier of predetermined length; and
   a plurality of expansile fibers fixed to the carrier at spaced intervals along the length of the carrier, the fibers being formed from an expansile polymer hydrogel.

9. The embolization device of claim 8, wherein the polymer hydrogel is of a type that expands in response to a change in an environmental parameter selected from the group consisting of temperature and pH after a predetermined time interval.

10. The embolization device of claim 8, wherein the carrier is configured in the form of a multi-looped structure that may assume a three-dimensional shape when unconstrained.

11. The embolization device of claim 10, wherein the three-dimensional shape is selected from the group consisting of a sphere, a helix, and an ovoid.

12. A vascular embolization device, comprising:
   a flexible, filamentous carrier having an exterior surface and a distal tip; and
   an expansile embolizing element non-releasably fixed coaxially to the exterior surface of the carrier at a location proximal from the distal tip, wherein the embolizing element is formed of an expansile, hydrophilic polymer that changes its physical character in response to a change in an environmental parameter selected from the group consisting of pH and temperature after a predetermined time interval.

13. The device of claim 12, wherein the carrier is formed of a flexible material having an elastic memory.

14. The device of claim 12, wherein the embolizing element is a first embolizing element fixed to the carrier at a cation, and wherein the device further comprises at least a second expansile embolizing element non-releasably fixed coaxially to the exterior surface of the carrier at a second location proximal from the distal tip.

15. The device of claim 12, wherein the carrier is configured in the form of a multi-looped structure that may assume a three-dimensional shape when unconstrained.

16. The device of claim 15, wherein the three-dimensional shape is selected from the group consisting of a sphere, a helix, and an ovoid.

17. The device of claim 12, wherein the embolizing element is formed of a stretch-resistant, biocompatible polymer.

18. The device of claim 12, wherein the embolizing element is expansible by a volumetric expansion factor of about 2× to about 100×.

19. The device of claim 12, wherein the polymer is a porous hydrogel.

20. A vascular embolization device that is deployable intravascularly while attached to a deployment instrument having a distal end, the embolization device comprising:
   a flexible filamentous carrier having proximal and distal ends;
   an embolizing element coaxially covering a substantial portion of the length of the carrier between the proximal and distal ends thereof, the embolizing element being formed of an expansile hydrophilic polymer that expands in response to a change in an environmental parameter; and
   a linkage element formed of an expansile hydrogel, located on the proximal end of the carrier, that releasably attaches the embolization device to the distal end of the deployment instrument.

21. A vascular embolization device that is deployable intravascularly while attached to a deployment instrument having a distal end, the embolization device comprising:
   a flexible filamentous carrier having proximal and distal ends;
   an embolizing element coaxially covering a substantial portion of the length of the carrier between the proximal and distal ends thereof, the embolizing element being formed of a stretch-resistant, expansile hydrophilic polymer that expands in response to a change in an environmental parameter; and
   a linkage element on the proximal end of the carrier that releasably attaches the embolization device to the distal end of the deployment instrument.

22. The embolization device of claim 21, wherein the carrier comprises a material that is visible under X-rays.

23. The embolization device of claim 21, wherein the polymer is an environmentally-sensitive polymer that changes its physical character in response to a change in an environmental parameter selected from the group consisting of temperature and pH.

24. The embolization device of claim 21, wherein the embolizing element is expansible by a volumetric expansion factor of between about 2× and about 100×.

25. The embolization device of claim 21, wherein the embolizing element is radiopaque.

26. The embolization device of claim 21, wherein the carrier is configured in the form of a multi-looped structure that may assume a three-dimensional shape when unconstrained.

27. The embolization device of claim 26, wherein the three-dimensional shape is selected from the group consisting of a sphere, a helix, and an ovoid.

28. A vascular embolization device that is deployable intravascularly while attached to a deployment instrument having a distal end, the embolization device comprising:
   a flexible filamentous carrier having proximal and distal ends;
   an embolizing element coaxially covering a substantial portion of the length of the carrier between the proximal and distal ends thereof, the embolizing element being formed of an expansile hydrophilic polymer that expands In response to a change in an environmental parameter selected from the group consisting of temperature and pH; and
   a linkage element on the proximal end of the carrier that releasably attaches the embolization device to the distal end of the deployment instrument.

29. The embolization device of claim 28, wherein the polymer is stretch-resistant.

30. The embolization device of claim 28, wherein the carrier comprises a material that is visible under X-rays.

31. The embolization device of claim 28, wherein the embolizing element is expansible by a volumetric expansion factor of between about 2× and about 100×.

32. The embolization device of claim 28, wherein the embolizing element is radiopaque.

33. The embolization device of claim 28, wherein the carrier is configured in the form of a multi-looped structure that may assume a three-dimensional shape when unconstrained.

34. The embolization device of claim 33, wherein the three-dimensional shape is selected from the group consisting of a sphere, a helix, and an ovoid.

* * * * *